United States Patent [19]
Swart

[11] Patent Number: 5,004,347
[45] Date of Patent: Apr. 2, 1991

[54] METHOD AND AN APPARATUS FOR INSPECTING THE EDGE OF A LID

[75] Inventor: Nicholaas C. Swart, Deventer, Netherlands

[73] Assignee: Heuft-Qualiplus B.V., Deventer, Netherlands

[21] Appl. No.: 439,591

[22] Filed: Nov. 20, 1989

[30] Foreign Application Priority Data

Nov. 21, 1988 [NL] Netherlands .................. 8802869

[51] Int. Cl.$^5$ ............................................. G01N 21/88
[52] U.S. Cl. .................................. 356/394; 356/237; 358/101; 358/106
[58] Field of Search ............... 356/394, 237; 358/101, 358/106; 382/8

[56] References Cited

U.S. PATENT DOCUMENTS 4,037,724 7/1977 Schultze et al. ............... 209/111.7
4,521,807 6/1985 Werson .............................. 358/106

FOREIGN PATENT DOCUMENTS 57-6306  1/1982 Japan .
57-7505  1/1982 Japan .
62-19738 1/1987 Japan .
2204125 11/1988 United Kingdom .

Primary Examiner—F. L. Evans
Attorney, Agent, or Firm—Willian Brinks Olds Hofer Gilson & Lione

[57] ABSTRACT

The invention has for its purpose to provide a method and an apparatus for inspecting the bent edge of a disc-shaped object, e.g. the annular edge of a metal lid bounding a gutter for sealing compound. In order to realize such an inspection with great reliability according to the invention the resolution is made as great as possible by means of the following steps:

(1) directing a light beam onto the edge zone of the object under an angle of incidents, such that the bent edge gives a shadow in said edge zone;
(2) previously determining the shape of the reflection picture also determined by said shadow of said illuminated edge zone in case of an object satisfying a predetermined standard;
(3) determining the reflection picture of the edge zone of an object to be inspected; and
(4) comparing the results of steps (3) and (4) and generating a rejection signal in case of a detected deviation lying outside a previously chosen tolerance range.

13 Claims, 1 Drawing Sheet

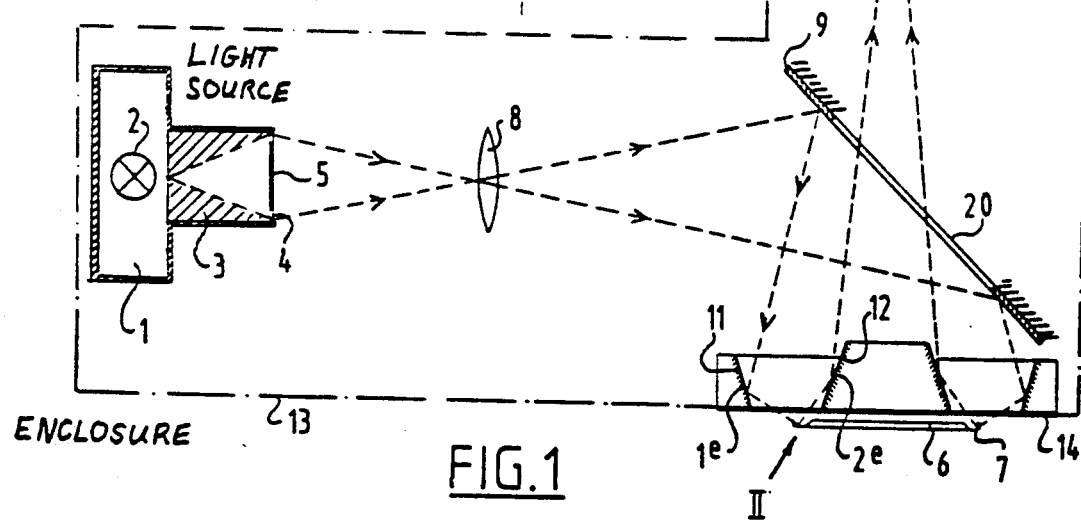

METHOD AND AN APPARATUS FOR INSPECTING THE EDGE OF A LID

The invention has for its purpose to provide a method and an apparatus for inspecting the bent edge of a disc-shaped object, e.g. the annular edge of a metal lid bounding a gutter for sealing compound.

In order to realize such an inspection with great reliability according to the invention the resolution is made as great as possible by means of the following steps:

(1) providing an object to be inspected;
(2) directing a light beam onto the edge zone of the object under an angle of incidence, such that the bent edge gives a shadow in said edge zone;
(3) previously determining the shape of the reflection picture also determined by said shadow of said illuminated edge zone in case of an object satisfying a predetermined standard;
(4) determining the reflection picture of the edge zone of an object to be inspected; and
(5) comparing the results of steps (4) and (3) and generating a rejection signal in case of a detected deviation lying outside a previously chosen tolerance range.

An apparatus for carrying out this method comprises:
(1) a light source;
(2) directing means for directing a light beam emitted by said light source on the edge zone such that the bent edge gives a shadow in that edge zone;
(3) memory means for storing the shape of the reflection picture of that illuminated edge zone, also determined by said shadow, in case of an object satisfying a previously determined standard;
(4) sensing means for determining the reflection picture of the edge zone of an object to be inspected; and
(5) comparing means for comparing the output signals of the sensing means and the memory means and for generating a rejection signal in case of a detected deviation lying outside a chosen tolerance range.

The invention will now be explained with reference to the accompanying drawing. In the drawing:

FIG. 1 is a schematic view of a first embodiment of an apparatus according to the invention;
FIG. 2 is the detail II of FIG. 1; and
FIG. 3 is a detail of an alternative embodiment.

FIG. 1 shows a light source 1 comprising a stroboscope lamp 2 and a conical light conductor 3 connected thereto. The light emitting end surface 4 of this conical light conductor 3 is matt and forms a strong annular light source. Inside the annular light emitting end edge a black screen 5 is arranged. For the construction of this light source reference is made to Dutch patent application 8800866 not published before, which patent application is hereby enclosed by way of reference.

The light emitted by the annular light source 4 is projected on a lid 6 to be inspected, and specifically on the annular gutter 7 thereof. Thereto use is made of a projection lense 8 and a mirror 9 having an elliptical hole 20 having a horizontal projection with the shape of a circle, and a first conical mirror 11.

As a result of the gutter 7 specifically shown in FIG. 2 and having an upstanding outer edge 8, on the bottom thereof a shadow is formed. The shadow-zone is in FIG. 2 indicated with 9.

If a part of the standing edge 8 of gutter 7 is lacking, the shadow zone 9 will be smaller. A video camera 10 senses the gutter 7 via the elliptical hole 20 in mirror 9. An observer viewing the picture picked up by camera 10 will hardly or not be able to see the annular gutter, unless the standing edge 8 of gutter 7 exhibits locally deviations, as a result of which the gutter will show illuminated parts.

By means of a second conical mirror 12 the illuminated area is observed with an appreciably enhanced brilliance, contributing to the detection-reliability.

Both mirrors 11, 12 are frosto-conical, the mirror 11 being internally reflecting and mirror 12 being externally reflecting.

For safeguarding the optical parts 1, 8, 9, 10, 11, 12 use is made of a closed enclosure 13 having a glass plate 14 serving as an inspection window. The mirrors 11 and 12 are arranged on this glass plate 14. Through glass plate 14 illumination and observation of the gutter 7 takes place.

The drawing do not show that transport or conveying means can be used for conveying successively underglass plate 4 a series of lids 6 to be inspected. The presence of a lid on the correct inspection position shown in FIG. 1 can trigger flash lamp 2, e.g. by means of an approach switch or the like, so that on the correct moment the video-camera 10 can sense the desired image.

FIG. 3 shows an alternative embodiment. Here use is made of a third conical mirror 15 causing a bundling of the annular picture of the gutter via a conical mirror 16 functionally corresponding with mirror 12 according to FIG. 1. By this arrangement as it were an optical magnification is achieved, as a result of which the resolution of the observation can substantially increase and the detection-accuracy can be enhanced.

The video signals coming from video-camera 10 are supplied to a signal processing unit 17 that can, if desired, control rejection means through an output 18. This signal processing unit 17 also comprises memory means for storing the shape of the reflection picture, also determined by the shadow according to FIG. 2, of the illuminated edge zone of the lid in case of a lid satisfying a predetermined standard. By means of comparing means also forming part of the signal processing unit 17 a comparison is made of the output signal of the video-camera 10 and the contents of the memory means. In case of a detected deviation outside a chosen tolerance range, an ejection signal is supplied via output 18. The related lid can in that case e.g. be ejected from the flow of conveyed objects by means of the above-mentioned, not-shown ejection means.

It should be noted that also use may be made of a continuous illumination, in which case a triggering of the video-camera takes place on the moment on which an object is located on the correct sensing position.

Furthermore it will be obvious that the shape of the light emitting edge 4 of light source 1 does not necessarily always have to be round, but can generally be adapted to any desired shape of the edge zone of an object to be inspected.

I claim:
1. A method for inspecting the bent edge of a lid comprising the steps of:
 placing the lid in a path of light;
 directing the light toward the bent edge of the lid, such that the bent edge casts a shadow onto the lid;
 monitoring the shadow of the bent edge of the lid;
 comparing the shadow of the bent edge of the lid with a reference to determine if the bent edge is flawed; and generating a rejection signal if the bent edge is flawed.

2. The method of claim 1 wherein the light is directed toward the bent edge using a conical mirror.

3. The method of claim 1 wherein the shadow is monitored using a video camera.

4. An apparatus for inspecting the bent edge of a lid, comprising:

a light source;

means for directing light emitted from the light source toward the bent edge of the lid, such that the bent edge casts a shadow onto the lid, the directing means being positioned between the light source and the lid;

means for monitoring the shadow of the bent edge;

means for storing a reference picture;

means for comparing the shadow of the bent edge with a reference to determine if the bent edge is flawed; and means for generating a rejection signal if the bent edge is flawed.

5. The apparatus of claim 4 wherein the means for directing the light from the light source toward the bent edge of the lid comprises a first mirror.

6. The apparatus of claim 5 wherein the first mirror is substantially conical.

7. The apparatus of claim 5 wherein the first mirror is internally reflecting.

8. The apparatus of claim 5 wherein the means for monitoring the shadow of the bent edge comprises a video camera.

9. The apparatus of claim 8 wherein the means for monitoring the shadow of the bent edge further comprises a second mirror positioned to reflect an image of the shadow toward the video camera.

10. The apparatus of claim 9 wherein the means for monitoring the shadow of the bent edge further comprises a third mirror positioned to reflect the image reflected by the second mirror into the video camera.

11. The apparatus of claim 10 wherein the third mirror is substantially conical.

12. The apparatus of claim 9 wherein the second mirror is substantially conical.

13. The apparatus of claim 9 wherein the second mirror is externally reflecting.

* * * * *

UNITED STATES PATENT AND TRADEMARK OFFICE
CERTIFICATE OF CORRECTION

PATENT NO. : 5,004,347

DATED : April 2, 1991

INVENTOR(S) : Nicholaas C. Swart

It is certified that error appears in the above-identified patent and that said Letters Patent is hereby corrected as shown below:

TITLE PAGE:

<u>IN THE ABSTRACT</u>

On line 17 of the Abstract, please delete "(3) and (4)" and substitute therefor --(2) and (3)--.

Signed and Sealed this

Twenty-second Day of September, 1992

*Attest:*

DOUGLAS B. COMER

*Attesting Officer*     *Acting Commissioner of Patents and Trademarks*